US011357556B2

(12) United States Patent
Frank et al.

(10) Patent No.: US 11,357,556 B2
(45) Date of Patent: Jun. 14, 2022

(54) ADJUSTABLE RIB AND STERNAL IMPLANT

(71) Applicant: Zimmer Biomet CMF and Thoracic, LLC, Jacksonville, FL (US)

(72) Inventors: Zach Frank, Jacksonville, FL (US); Anish Vaghela, Jacksonville, FL (US); Scott Sidwell, Fleming Island, FL (US); Ryan Luby, Ponte Vedra Beach, FL (US); Kyle Icke, Jacksonville, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 289 days.

(21) Appl. No.: 16/689,587

(22) Filed: Nov. 20, 2019

(65) Prior Publication Data

US 2020/0085476 A1    Mar. 19, 2020

Related U.S. Application Data

(63) Continuation of application No. 15/403,972, filed on Jan. 11, 2017, now Pat. No. 10,543,027.

(51) Int. Cl.
| | | |
|---|---|---|
| *A61B 17/80* | (2006.01) | |
| *A61B 34/10* | (2016.01) | |
| *A61B 17/04* | (2006.01) | |
| *A61F 2/08* | (2006.01) | |

(52) U.S. Cl.
CPC ...... *A61B 17/8076* (2013.01); *A61B 17/8023* (2013.01); *A61B 2017/0414* (2013.01); *A61B 2017/0464* (2013.01); *A61B 2034/108* (2016.02); *A61F 2002/0829* (2013.01)

(58) Field of Classification Search
CPC .............. A61B 17/842; A61B 17/8076; A61B 17/823
See application file for complete search history.

(56) References Cited

U.S. PATENT DOCUMENTS

| | | | |
|---|---|---|---|
| 8,556,948 | B2 | 10/2013 | Teague et al. |
| 9,265,543 | B2 | 2/2016 | Gephart |
| 9,339,388 | B2 | 5/2016 | Dartevelle |
| 10,543,027 | B2 | 1/2020 | Frank et al. |

(Continued)

FOREIGN PATENT DOCUMENTS

| | | |
|---|---|---|
| CN | 202386768 U | 8/2012 |
| CN | 106109057 A | 11/2016 |

(Continued)

OTHER PUBLICATIONS

"U.S. Appl. No. 15/403,972, Advisory Action dated Jan. 30, 2019", 2 pgs.

(Continued)

*Primary Examiner* — Matthew J Lawson
(74) *Attorney, Agent, or Firm* — Schwegman Lundberg & Woessner, P.A.

(57) ABSTRACT

An implant assembly for a human sternum and ribs can include a sternal implant and a rib link. The sternal implant can be couplable to a sternum. The rib link can include a distal portion, a proximal portion, and a strut. The distal portion can be couplable to a rib. The proximal portion can be couplable to the sternal implant. The strut can connect the distal portion to the proximal portion. The strut can be configured to flex so that the distal portion can be aligned with the rib.

20 Claims, 6 Drawing Sheets

(56) References Cited

U.S. PATENT DOCUMENTS

| | | | |
|---|---|---|---|
| 2003/0055429 A1* | 3/2003 | Ip | A61B 17/8085 606/284 |
| 2009/0248091 A1 | 10/2009 | Teague et al. | |
| 2014/0163691 A1 | 6/2014 | Dartevelle | |
| 2014/0257291 A1 | 9/2014 | Houff | |
| 2014/0350613 A1 | 11/2014 | Bardaji | |
| 2018/0036052 A1 | 2/2018 | Fabre et al. | |
| 2018/0193073 A1 | 7/2018 | Frank et al. | |

FOREIGN PATENT DOCUMENTS

| | | |
|---|---|---|
| CN | 106264794 A | 1/2017 |
| CN | 110191687 A | 8/2019 |
| EP | 0583520 A1 | 2/1994 |
| FR | 3004337 A1 | 10/2014 |
| JP | H04231948 A | 8/1992 |
| JP | H0690962 A | 4/1994 |
| JP | 2013532499 A | 8/2013 |
| WO | WO-2016034778 A1 | 3/2016 |
| WO | 2016135395 | 9/2016 |
| WO | WO-2016207255 A1 | 12/2016 |
| WO | WO-2018132179 A1 | 7/2018 |

OTHER PUBLICATIONS

"U.S. Appl. No. 15/403,972, Examiner Interview Summary dated Aug. 16, 2019", 3 pgs.
"U.S. Appl. No. 15/403,972, Final Office Action dated Nov. 9, 2018", 12 pgs.
"U.S. Appl. No. 15/403,972, Non Final Office Action dated May 24, 2019", 12 pgs.
"U.S. Appl. No. 15/403,972, Non Final Office Action dated Aug. 6, 2018", 15 pgs.
"U.S. Appl. No. 15/403,972, Notice of Allowance dated Sep. 18, 2019", 5 pgs.
"U.S. Appl. No. 15/403,972, Response filed Jan. 9, 2019 to Final Office Action dated Nov. 9, 2018", 10 pgs.
"U.S. Appl. No. 15/403,972, Response filed Oct. 10, 2018 to Non Final Office Action dated Aug. 6, 2018", 13 pgs.
"U.S. Appl. No. 15/403,972, Response filed Aug. 23, 2019 to Non-Final Office Action dated May 24, 2019", 10 pgs.
"International Application Serial No. PCT/US2017/062234, International Preliminary Report on Patentability dated Jul. 25, 2019", 8 pgs.
"International Application Serial No. PCT/US2017/062234, International Search Report dated Mar. 15, 2018", 5 pgs.
"International Application Serial No. PCT/US2017/062234, Written Opinion dated Mar. 15, 2018", 6 pgs.
Hipolite, Whitney, "Woman With the Metal Chest: Surgeons Implant World's First 3D Printed Titanium Sternum", (Jul. 9, 2015), 5 pgs.
Quick, Darren, "Patient receives 3D-printed titanium sternum and rib cage", (Sep. 10, 2015), 5 pgs.
"Australian Application Serial No. 2017393185, First Examination Report dated Dec. 23, 2019", 3 pages.
"European Application Serial No. 17817371.2, Response to Communication pursuant to Rules 161(1) and 162 EPC filed Feb. 19, 2020", 12 pages.
"Australian Application Serial No. 2017393185, Response filed Feb. 28, 2020 to First Examination Report dated Dec. 23, 2019", 14 pages.
"Canadian Application Serial No. 3,049,634, Office Action dated Jan. 18, 2021", 3 pgs.
"Canadian Application Serial No. 3,049,634, Office Action dated Aug. 12, 2020", 4 pgs.
"Canadian Application Serial No. 3,049,634, Response filed May 12, 2021 to Office Action dated Jan. 18, 2021", 10 pgs.
"Canadian Application Serial No. 3,049,634, Response filed Dec. 10, 2020 to Office Action dated Aug. 12, 2020", 13 pgs.
"Chinese Application Serial No. 201780083083.7, Office Action dated Jun. 29, 2021", W/English Translation, 15 pgs.
"Chinese Application Serial No. 201780083083.7, Response filed Oct. 22, 2021 to Office Action dated Jun. 29, 2021", w/ English claims, 21 pgs.
"Japanese Application Serial No. 2019-537774, Notification of Reasons for Refusal dated Jul. 14, 2020", w/ English translation, 6 pgs.
"Japanese Application Serial No. 2019-537774, Response filed Oct. 13, 2020 to Notification of Reasons for Refusal dated Jul. 14, 2020", w/ English claims, 11 pgs.

* cited by examiner

ADJUSTABLE RIB AND STERNAL IMPLANT

CLAIM OF PRIORITY

This application is a continuation of U.S. patent application Ser. No. 15/403,972, filed on Jan. 11, 2017, the benefit of priority of which is claimed hereby, and which is incorporated by reference herein in its entirety.

BACKGROUND

For patients with a sternal tumor, congenital sternal disorder, or various sternal injuries surgeons sometimes remove an affected sternum or sternal portion. Depending on the location and size of the tumor, adjoining rib segments can be disconnected from the sternum as part of the procedure. For regaining the anatomical integrity between the sternum and rib cage and for protecting the organs that are directly behind the sternum, surgeons can use a muscle flap to provide coverage and protection of the affected rib segments and sternum. In cases where a large section or the total sternum is removed, these muscle flaps may not offer the protection and support needed for maintaining the anatomical integrity.

OVERVIEW

In cases where a large section of a sternum is removed or missing, the inventors have recognized, among other things, that a sternal implant to replace a patient's sternum and/or manubrium can offer several advantages over a muscle flap or single plate method. In some examples, the implant can include removable rib links that are individually couplable to ribs. In some examples, the implant can also include superior bores for securing the sternal implant to remaining sternum bone and/or manubrium. The implant can also include cartilage connectors for securing the implant to costal cartilage. This design can provide structural rigidity and organ protection not provided by a muscle flap method. This design can also provide flexibility, adaptability, and modularity not provided by a single-plate method.

To further illustrate the apparatuses and systems disclosed herein, the following non-limiting examples are provided:

Example 1 is an implant assembly for a human sternum and ribs, the implant assembly comprising: a sternal implant couplable to a sternum; and a first rib link comprising: a distal portion couplable to a rib; a proximal portion couplable to the sternal implant; and a strut connecting the distal portion to the proximal portion, the strut configured to flex so that the distal portion can be aligned with the rib.

In Example 2, the subject matter of Example 1 optionally includes a plurality of rib links including the first rib link, each of the plurality of rib links releasably couplable to the sternal implant.

In Example 3, the subject matter of any one or more of Examples 1-2 optionally include wherein the sternal implant further comprises: a superior portion securable to the sternum; an inferior portion securable to costal cartilage; and a matrix portion disposed between the superior and inferior portions, and configured to receive the proximal portion of the first rib link.

In Example 4, the subject matter of Example 3 optionally includes a plurality of rib links including the first rib link, each of the plurality of rib links releasably couplable to the matrix portion.

In Example 5, the subject matter of Example 4 optionally includes wherein the matrix portion is configured to receive a proximal portion of each of the plurality of rib links.

In Example 6, the subject matter of Example 5 optionally includes wherein the matrix portion is configured to receive the proximal portions in various locations as desired.

In Example 7, the subject matter of any one or more of Examples 3-6 optionally include wherein the distal portion of the sternal implant further comprises: a first cartilage link extending from the inferior portion, the cartilage link including a plurality of suture bores.

In Example 8, the subject matter of Example 7 optionally includes wherein the inferior portion of the sternal implant further comprises: a plurality of cartilage links including the first cartilage link, each of the plurality of cartilage links extending from the inferior portion and including a plurality of suture bores.

In Example 9, the subject matter of any one or more of Examples 1-8 optionally include wherein the strut comprises a cylindrical geometry.

In Example 10, the subject matter of any one or more of Examples 1-9 optionally include wherein the distal portion comprises: an alignment tab extending from the distal portion configured to at least partially engage the rib to align the distal portion with the rib.

In Example 11, the subject matter of any one or more of Examples 1-10 optionally include wherein the distal portion comprises: a posterior surface mateable to the rib and comprising a patient-matched topography.

In Example 12, the subject matter of any one or more of Examples 1-11 optionally include wherein the distal portion comprises: a plurality of bores configured to receive bone fasteners, the plurality of bores staggered across the distal portion to distribute stress transferred between the rib and the distal portion.

Example 13 is a sternal and rib replacement system comprising: a sternal implant couplable to a sternum; and a plurality of rib links, each rib link comprising: a distal portion couplable to a rib; a proximal portion couplable to the sternal implant; and a strut connecting the distal portion to the proximal portion, the strut configured to flex so that the distal portion can be aligned with the rib.

In Example 14, the subject matter of Example 13 optionally includes wherein the sternal implant further comprises: a superior portion securable to the sternum; an inferior portion securable to costal cartilage; and a matrix portion disposed between the superior and inferior portions, and configured to receive the proximal portion of the first rib link.

In Example 15, the subject matter of Example 14 optionally includes wherein the matrix portion is configured to receive a proximal portion of each of the plurality of rib links in various locations as desired.

In Example 16, the subject matter of any one or more of Examples 14-15 optionally include wherein the inferior portion of the sternal implant further comprises: a plurality of cartilage links including the first cartilage link, each of the plurality of cartilage links extending from the distal portion and including a plurality of suture bores.

In Example 17, the subject matter of any one or more of Examples 13-16 optionally include wherein the strut comprises a cylindrical geometry.

In Example 18, the subject matter of any one or more of Examples 13-17 optionally include wherein the distal portion comprises: an alignment tab extending from the distal portion and configured to partially engage the rib to align the distal portion with the rib.

In Example 19, the subject matter of any one or more of Examples 13-18 optionally include wherein the distal portion comprises: a posterior mating surface mateable to the rib and comprising a patient-matched topography.

In Example 20, the subject matter of any one or more of Examples 13-19 optionally include wherein the distal portion comprises: a plurality of bores configured to receive bone fasteners, the plurality of bores staggered across the distal portion to distribute stress transferred between the rib and the distal portion.

In Example 21, the subject matter of any one or more of Examples 1-12 optionally include a fastener securing the proximal portion to the sternal implant.

In Example 22, the subject matter of any one or more of Examples 1-12 and 21 optionally wherein the fastener is a locking screw.

In Example 23, the subject matter of any one or more of Examples 1-12 and 21-22 optionally wherein the fastener comprises an anti-rotation cap configured to prevent the fastener from backing out of the proximal portion.

In Example 24, the subject matter of any one or more of Examples 1-12 and 21-22 optionally include an anti-rotation tab adjacent a head of the fastener, the anti-rotation tab configured to prevent the fastener from backing out of the proximal portion.

In Example 24, the subject matter of any one or more of Examples 1-12 and 21-24 optionally include a plasma coating applied to one or more of the sternal implant and the first rib link.

In Example 25, the subject matter of any one or more of Examples 13-20 optionally include a fastener securing the proximal portion to the sternal implant.

In Example 26, the subject matter of any one or more of Examples, 13-20 and 25 optionally wherein the fastener is a locking screw.

In Example 27, the subject matter of any one or more of Examples 13-20 and 25-26 optionally wherein the fastener comprises an anti-rotation cap configured to prevent the fastener from backing out of the proximal portion.

In Example 28, the subject matter of any one or more of Examples 13-20 and 25-26 optionally include an anti-rotation tab adjacent a head of the fastener, the anti-rotation tab configured to prevent the fastener from backing out of the proximal portion.

In Example 29, the subject matter of any one or more of Examples 13-20 and 25-28 optionally include a plasma coating applied to one or more of the sternal implant and the first rib link.

Example 30 is an implant assembly for a human sternum and ribs, the implant assembly comprising:
a sternal implant couplable to a sternum; and a first rib link comprising: a distal portion couplable to a rib; a proximal portion couplable to the sternal implant; and a strut connecting the distal portion to the proximal portion, the strut configured to flex so that the distal portion can be aligned with the rib; and a lag tool comprising a proximal end and a distal end, the distal end threadably engageable with the sternal implant.

In Example 31, the subject matter of Example 30 optionally includes wherein the distal end is sized to pass through a bore of the distal portion to lag the distal portion to the sternal implant In Example 32, the subject matter of any one or more of Examples 30-31 optionally includes a collar disposed at a termination of the threading and configured to contact the proximal end and force the proximal end towards the sternal implant as the lag tool threadably couples to the sternal implant.

In Example 33, the subject matter of any one or more of Examples 30-32 optionally includes a tool interface disposed near the proximal end of the lag tool and coupleable to a driver.

In Example 34, the subject matter of any one or more of Examples 30-33 optionally includes wherein the tool interface comprises a circumferential groove.

These and other examples and features of the present apparatuses and systems will be set forth in part in the following Detailed Description. This Overview is intended to provide non-limiting examples of the present subject matter and it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems for sternal replacement procedures. For example, the present application discloses a sternal and rib implant system configured to secure to a sternum, manubrium, and/or ribs of a patient. Details are discussed further below.

Figure 1:
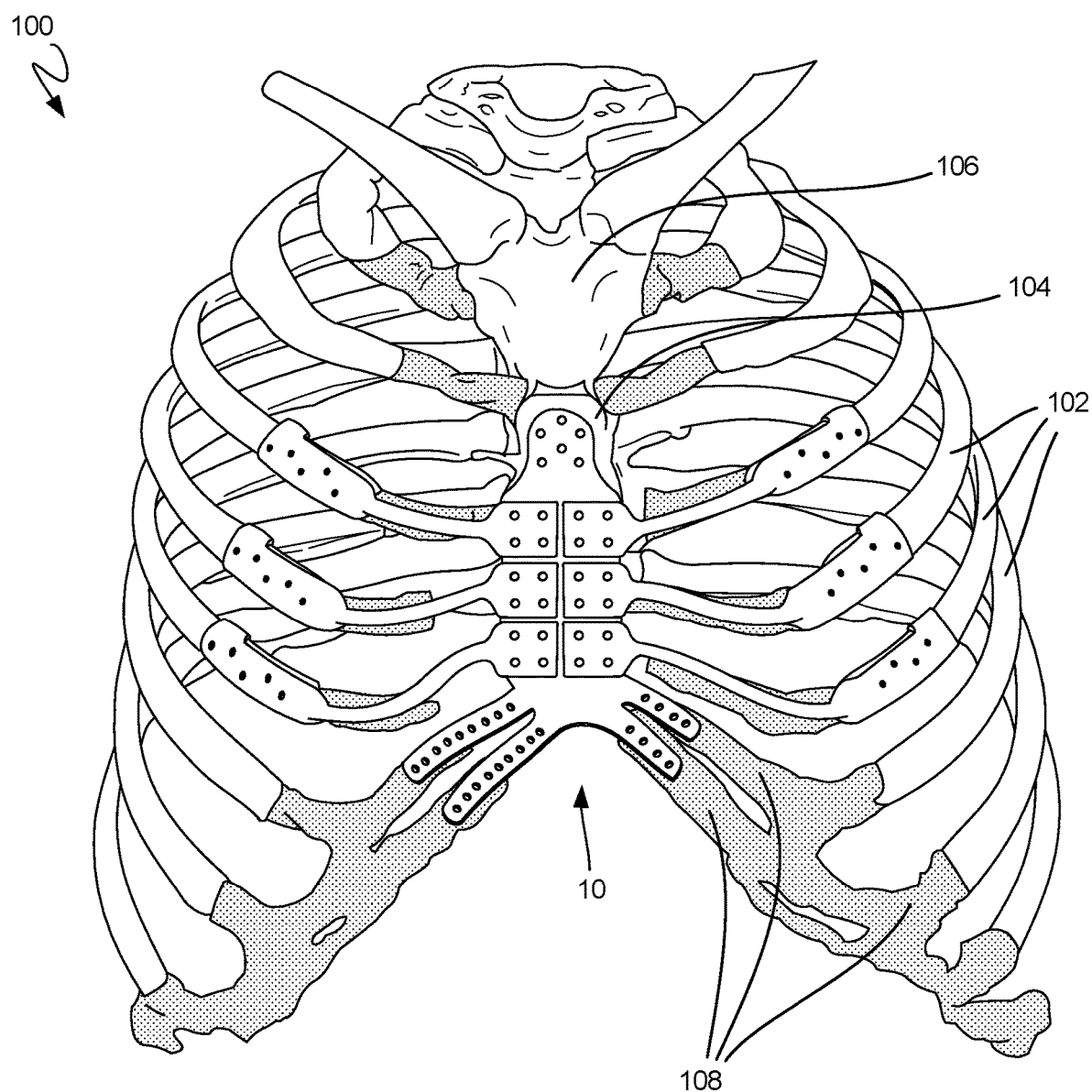
FIG. 1 shows an isometric view of a rib and sternal implant coupled to a rib cage of a patient, in accordance with an example of the present disclosure.

FIG. 1 shows an isometric view of implant 10 secured to rib cage 100 of a patient, in accordance with an example of the present disclosure. Rib cage 100 generally includes ribs 102, sternum (or body) 104, manubrium (or upper sternum) 106, and cartilage (or costal cartilage) 108. Rib cage 100 generally includes other components not labeled or shown, such as a xyphoid process.

In some patients, a sternum, such as sternum 100 can become compromised, such as with a tumor. In some of these cases, the sternum, manubrium, xyphoid process, ribs, and/or cartilage may need to be removed or disconnected by a surgeon. In many of such cases, implant 10 can be used to replace the removed structural components, such as sternum 104 and manubrium 106.

In some examples, implant 10 can be a sternal implant coupled to a resected or partial sternum 104 and/or manubrium 106 at a superior portion and coupled to cartilage 108 at an inferior and/or distal portion, or at any location of a patient where cartilage is present in a patient. Implant 10 can also include rib links coupled to a matrix of the implant, where the rib links can be further coupled to ribs 102.

Once connected, in some examples, implant 10 can provide some of the structure and functions lost as a result of resecting or removing sternum 104, manubrium 106, and/or ribs 102, such as protecting vital organs. Though other implants exist in the prior art, implant 10 provides the benefit of modularity as rib links can be installed in many configurations. Implant 10 also offers the benefit of customization, as implant 10 can be patient-matched in many ways. These details and more are discussed further below.

Figure 2:
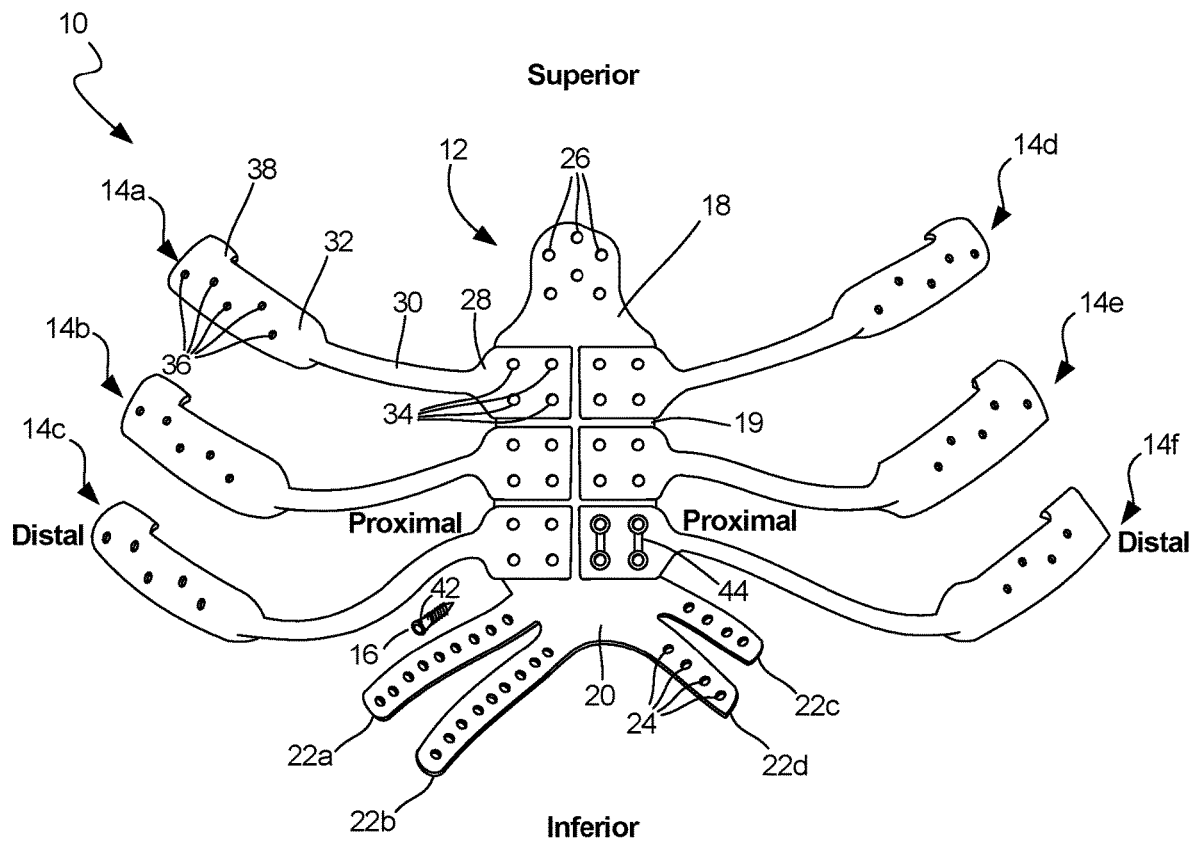
FIG. 2 shows an isometric view of a rib and sternal implant from an anterior perspective, in accordance with an example of the present disclosure.
Figure 3:
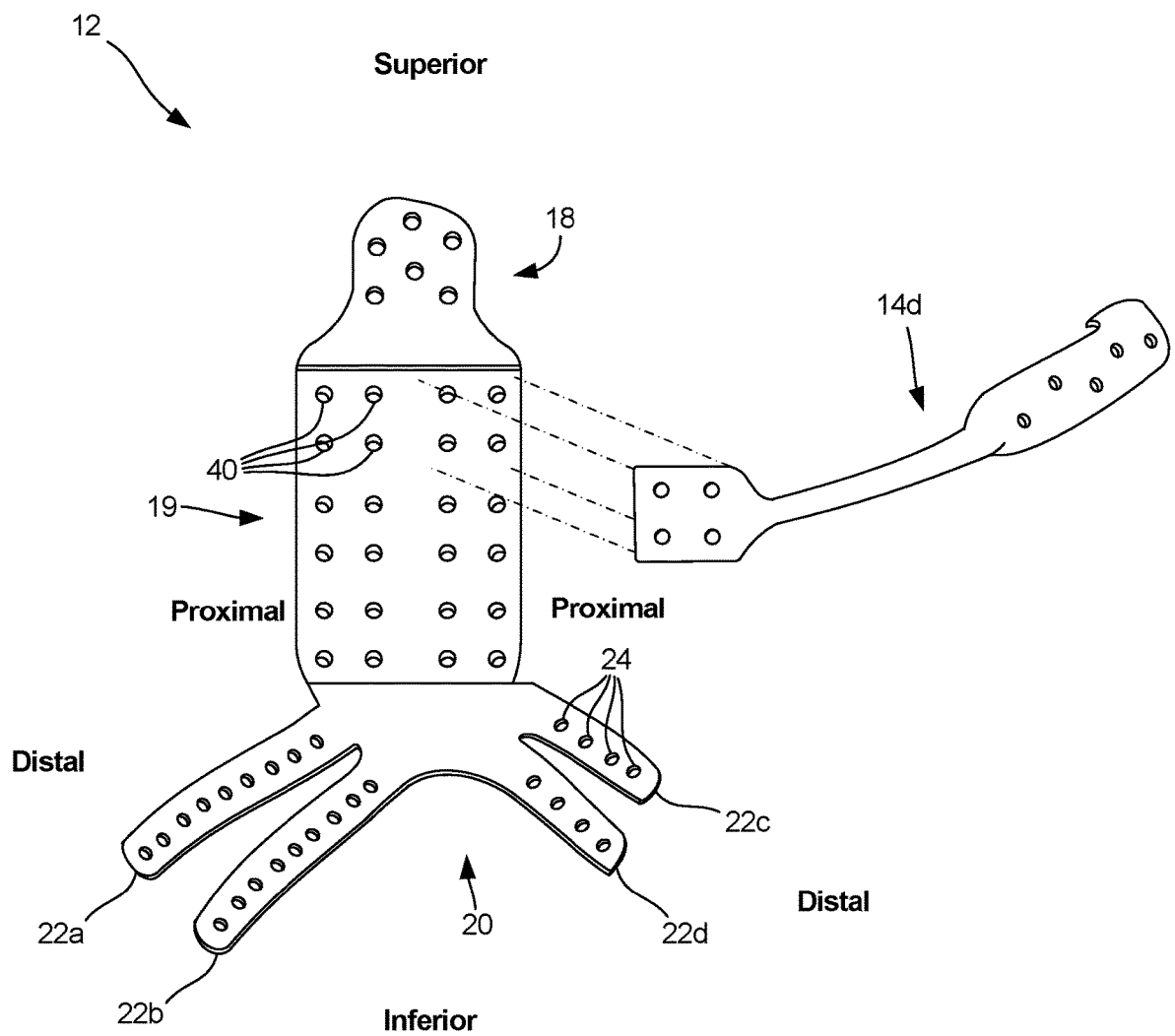
FIG. 3 shows an isometric view of a sternal implant from an anterior perspective, in accordance with an example of the present disclosure.

FIG. 2 shows an isometric view of implant 10 from an anterior perspective. FIG. 3 shows an isometric view of implant 10 with rib links removed. FIGS. 2 and 3 are discussed concurrently.

Implant 10 can include sternal implant 12, rib links 14*a*, 14*b*, 14*c*, 14*d*, 14*e*, and 14*f*, and fasteners 16. Sternal implant 12 can include superior portion 18, matrix 19, and inferior portion 20. Inferior portion 20 can include cartilage links 22*a*, 22*b*, 22*c*, and 22*d*, which can each include suture bores 24. Superior portion can include superior bores 26. Each of rib links 14*a*-14*f* can include proximal portion 28, strut 30, and distal portion 32. Each of proximal portions 28 can include proximal bores 34. Each of distal portions 32 can include distal bores 36, and alignment tabs 38. Matrix 19 can include matrix bores 40. Fasteners 16 can include cap 42 in some examples and can include tang 44 in some other examples. Also shown in FIGS. 2 and 3 are orientation identifiers superior, inferior, proximal, and distal.

Sternal implant 12 and rib links 14 can be comprised of a rigid material, such as any material suitable for implant in a human body, for example, stainless steel alloys, titanium alloys, polyetherketoneketone (PEKK), and cobalt/chromium alloys. In one example, sternal implant 12 and rib link 14 can be comprised of titanium 6Al-4V.

Sternal implant 12 can be of a geometric shape of a sternum and/or a manubrium. In some examples, sternal implant 12 can have a shape that is matched to a native anatomy, such as a sternum, of a patient. This can improve the overall fit and comfort of implant 10, and can simplify installation of implant 10.

In some examples, superior portion 18 can extend superiorly from matrix 19 of sternal implant 12. In other examples, superior portion 18 can extend in other directions from matrix 19, such as distally or inferiorly, depending on anatomical requirements of a patient. Further, superior portion 18 can be placed at any location on sternal implant 12, as required by the anatomy of a patient.

Superior portion 18 can be coupled to a sternum, such as sternum 104 of FIG. 1, or a manubrium, such as manubrium 106 of FIG. 1. Inferior portion 20 can extend inferiorly and/or distally from matrix 19, in some examples, and can extend in any direction from matrix 19 in other examples. In some examples, each of cartilage links 22 can extend inferiorly and/or distally from inferior portion 20, with suture bores 24 spaced along each of cartilage links 22. Suture bores 24 can be sized and spaced to accept sutures, allowing cartilage links 22 to be coupled to costal cartilage, such as cartilage 108 of FIG. 1. In some examples, suture bores 24 can be sized to accept bone screws or other fasteners, for securing one of cartilage links 22 to a bone, such as a rib or other bone, depending on the anatomy of a patient. In some examples, cartilage links 22 can be separate pieces, securable to sternal implant 12 with fasteners. This can provide additional modularity, similar to that provided by rib links 14, as discussed below.

Superior bores 26 can be sized to accept bone screws or other bone fasteners, so that superior portion 18 can be coupled to a sternum and/or a manubrium. Superior bores can be placed about superior portion 18 to optimize fastening as a function of the remaining anatomy. In some examples, superior bores 26 can be sized to accept sutures, depending on the anatomy of a patient.

Rib links 14*a*-14*f* can be attached and removed from sternal implant 12, as shown in FIG. 3. Rib links 14*a*-14*f* can have a length and curvature configured to match a natural anatomy of a given patient. In some examples, rib links 14*a*-14*f* can be modified in shape during a procedure for improved fitment, as described further below. Though six of rib links 14*a*-14*f* are shown, other quantities, such as 1, 2, 3, 4, 5, 10, and the like can be used. In some examples, a quantity of rib links can be selected pre-operatively or intra-operatively to match patient anatomy or surgical needs.

Proximal portions 28 of rib links 14*a*-14*f* can each removably couple to matrix 19 of sternal implant 12 using matrix bores 40 of sternal implant 12 and proximal bores 34 of proximal portions 28. In some examples, fasteners, such as fasteners 16, which can be metallic or polymeric screws or bolts having a machine thread type, can pass through proximal bores 34 to threadably engage matrix bores 40. In some examples, fasteners 16 can be bone screws or other suitable fasteners. Heads of fasteners 16 can apply a force to proximal portion 28 to secure proximal portion 28 to matrix 19. In some examples, cap 42 can be coupled to a head of one or more of fasteners 16 to prevent fasteners 16 from backing out of matrix bores 40 and proximal bores 34 and to provide a smooth surface on top of fasteners 16. Additionally or alternatively, tang 44 can span the heads of two of fasteners 16 to prevent backing out.

In some other examples, snap connections can be used to connect proximal portion 28 to matrix 19. The snap connections can comprise various geometric shapes configured to mate to bores of various geometric shapes. In one example, one or more metal or plastic prongs can extend from proximal portion 28 and extend into a matrix bore 40 and once the prong(s) has extended partially through a matrix bore 40, a protrusion on the end of the prong(s) can snap into a recess in the matrix bore 40. Alternatively, a protrusion on the end of the prong(s) can extend all the way through matrix bore 40 and snap outwardly once the prong(s) has penetrated all the way through matrix bore 40. In some other examples, the one or more prongs or snap connections can extend from matrix 19 and penetrate bores 34, to yield a snap connection similar to that described above. In some of these examples, a cap can be installed on the top or the bottom of the snap and/or its mating bore to create a smooth anterior surface of proximal portion 28 or posterior surface of matrix 19. In some of these examples, the snaps can be comprised of a temperature dependent shape memory alloy, such as Nitinol, so that rib links 14*a*-14*f* can be placed on matrix 19 as desired during surgery, and provide a provisional connection which can be adjusted during surgery, but can take a different shape to secure proximal portion 28 to matrix 19 as the surgery proceeds or ends and as the temperature of the snap reaches the body temperature of the patient.

In some examples, fasteners 16 or snaps, can be integrated or captivated to one or more of proximal portion 28 and/or matrix 19. In some examples, fasteners 16 can be captivated to proximal portion 28 such that fasteners 16 are pre-installed in proximal portion 28 but are not able to back out of proximal portion 28, yet are able to be rotated and thereby advance through proximal bores 34 and into matrix bores 40. In an example, fasteners 16 can be partially threaded into proximal bores 34 and thereby be housed in proximal bores 34 prior to surgery, and be ready for advancement into matrix bore 40 during surgery, for example. In an example, fasteners 16 can be retained in proximal bores 34 using, for example, an o-ring. Fasteners 16 can be captivated such that fasteners 16 do not extend past a posterior surface of proximal portion 28 where a force directed towards matrix 19 is required to release fasteners 16 for engagement with matrix bores 40. In this way, fasteners 16 may not interfere with the placement of proximal portion 28 on matrix 19.

In some examples, portions of matrix 19 and/or proximal portion 28, and/or the fasteners 16 themselves can comprise a magnetized material. In operation of some of these examples, magnetic portions of matrix 19 and/or proximal portion 28 can attract fasteners 16, preventing fasteners from falling into a patient's thoracic cavity during a surgical operation.

In some examples, matrix bores 40 can be of a quantity that is equal to a quantity of all of proximal bores 34, providing a predetermined configuration for attaching rib links 14 to sternal implant 12, which can save time in procedures. In some other examples, matrix bores can be of a quantity that is larger than a quantity of all of proximal bores 34, so that proximal portions 28 can be coupled to matrix 19 in various configurations. This variation offers intra-operative flexibility that enables a physician to place rib links 14 relative to sternal implant 12 in a configuration that matches anatomy of a patient, as desired.

Distal portions 32 of each of rib links 14a-14f can couple to ribs, such as ribs 102 of FIG. 1, using distal bores 36. Distal bores 36 can be sized to accept bone screws or other bone fasteners to secure rib links 14a-14f to ribs. In some examples, distal bores 36 can be configured to accept sutures. In some examples, distal bores 36 can be staggered about distal portions 32 so that stresses or forces transferred between distal portions 32 and ribs can be distributed throughout the ribs and distal portions 32. This can help prevent fracturing of distal portions 32 and can help prevent fracturing of ribs.

Alignment tabs 38 (or locating tabs or positioning tabs) can be integral to distal portions 32 and can be disposed at a distal termination along a superior edge of distal portions 32. In other examples, alignment tabs 38 can be located along any other edge of distal portions 32. Alignment tabs 38 can extend superiorly from the distal portions 32 and can curve superiorly and posteriorly. In this manner, alignment tabs 38 can be curved to partially engage a rib, helping to position distal portion 32 in parallel or coaxial alignment with the rib.

Strut 30 can connect distal portion 32 to proximal portion 28 for each of rib links 14a-14f. Strut 30 can have a cylindrical geometric shape, in some examples, and can have other geometric shapes, such as a rectangular prism, and the like, in other examples. Struts 30 can be hollow or solid in cross-section. In some examples, the cylindrical geometric shape of strut 30 can allow for distal portion 32 and proximal portion 28 to be moved relative to each other. The cylindrical geometry of struts 30 can allow for bending of strut 30 in any direction or any plane, for example using a rod bender. This can enable surgeons to make minor adjustments in locating distal portions 32 relative to the ribs during a procedure, or proximal portions 28 relative to matrix 19. This flexibility and adjustability can overcome the disadvantage of having to fracture ribs to align ribs with a single piece plate that is not adjustable.

Though matrix bores 40, suture bores 24, and superior bores 26 are shown in specific locations on sternal implant 12, these bores can be placed in any location on sternal implant 12 to align with a patient's anatomy.

Figure 4:
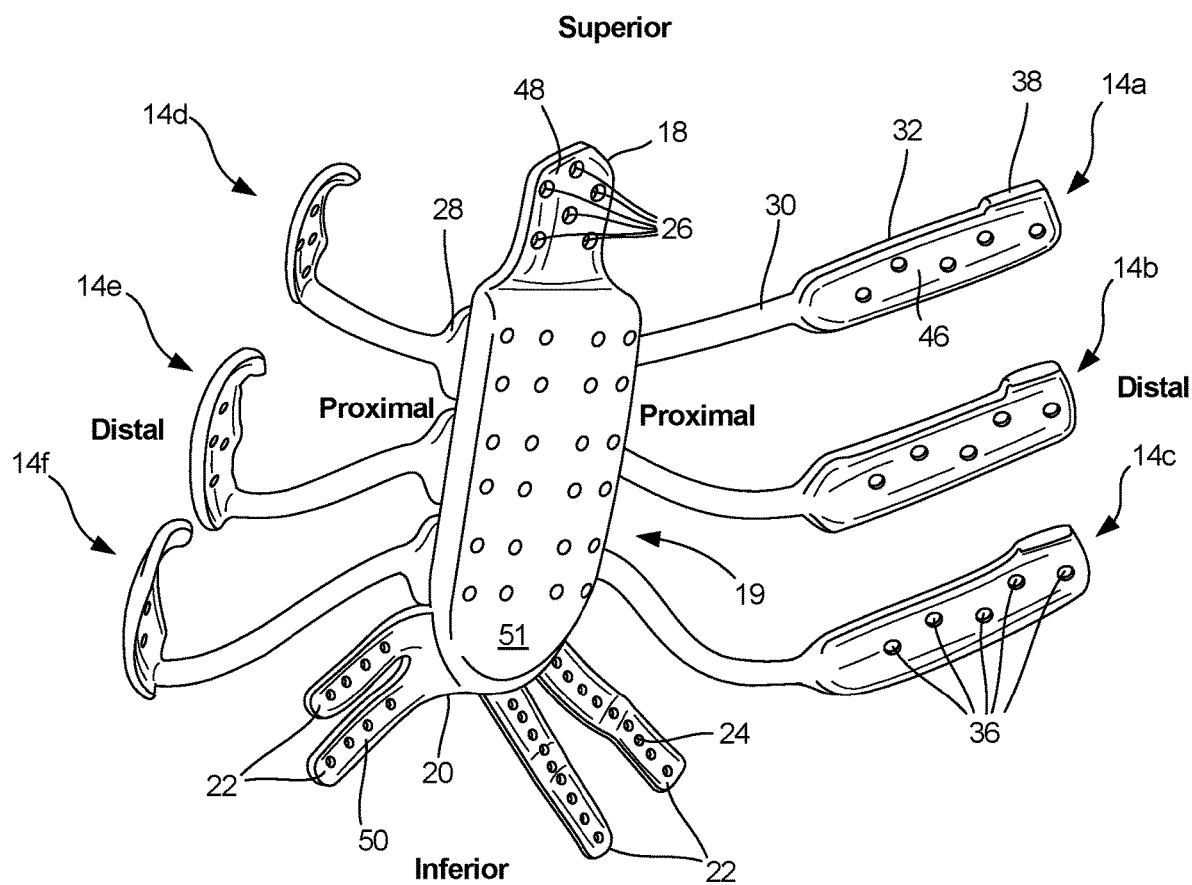
FIG. 4 shows an isometric view of a rib and sternal implant from a posterior perspective, in accordance with an example of the present disclosure.

FIG. 4 shows an isometric view of implant 10 from a posterior perspective, in accordance with an example of the present disclosure. Implant 10 can include sternal implant 12, rib links 14a, 14b, 14c, 14d, 14e, and 14f. Sternal implant 12 can include superior portion 18, matrix 19, and inferior portion 20. Inferior portion 20 can include cartilage links 22, which can include suture bores 24. Superior portion can include superior bores 26. Each of rib links 14a-14f can include proximal portion 28, strut 30, and distal portion 32. Each of distal portions 32 can include distal bores 36, and alignment tabs 38. Also shown in FIG. 4 are orientation identifiers superior, inferior, proximal, and distal.

The components of FIG. 4 can be connected and operate consistently with FIGS. 1-3. However, FIG. 4 shows additional details of implant 10, such as rib mating surface 46 of rib links 14a-14f, superior mating surface 48 of superior portion 18, cartilage mating surface 50 of cartilage links 22, and sternal mating surface 51 of matrix 19. To the extent there is a portion of sternum remaining, the sternal mating surface 51 may be attached to the portion of the sternum using fasteners 16 and matrix bores 40, for example.

Rib mating surface 46 can be a posterior surface of distal portion 32 of each of rib links 14a-14f. Superior mating surface 48 can be a posterior surface of superior portion 18 of sternal implant 12. Cartilage mating surface 50 can be a posterior surface of each of cartilage links 22.

Each of rib mating surface 46, superior mating surface 48, and cartilage mating surface 50 can have a surface topography that is matched to the bones and tissues of a patient so that the bone can conform to the mating surface of the bone and/or tissue. This can provide better fit, adhesion, ingrowth, a higher friction interface, and comfort of implant 10.

Additionally or alternatively, each of rib mating surface 46, superior mating surface 48, cartilage mating surface 50, and/or sternal mating surface 51 can receive a porous titanium plasma spray coating. This coating can promote ingrowth and provide a higher friction interface between the components of implant 10 and the mating bone and/or tissue. These benefits can provide secondary benefits such as better stability and can reduce a load on fasteners 16 and bone fasteners, which can prevent future procedures, saving cost and improving quality of life. Additionally or alternatively, each of rib mating surface 46, superior mating surface 48, cartilage mating surface 50, and/or sternal mating surface 51 can comprise a textured surface, including concave dimples, convex protrusions, or small pin-like protrusions, for example, to aid in attachment and/or adhesion to bone and tissue.

FIG. 4 also shows how alignment tabs 38 can curve superiorly and posteriorly, such that alignment tabs 38 can engage a superior surface of ribs to position and align distal portions 32 relative to ribs 102.

Figure 5:
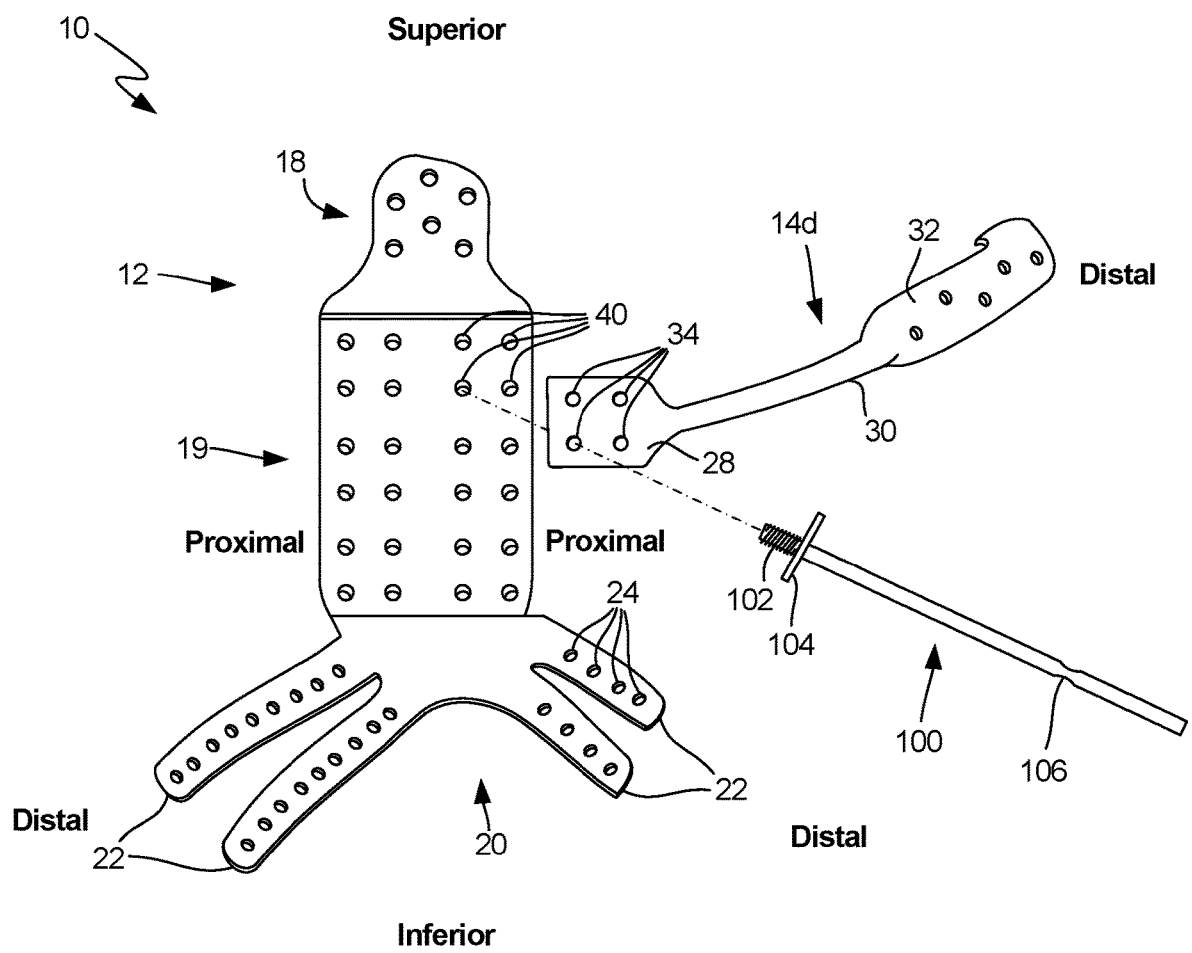
FIG. 5 shows an isometric view of a rib and sternal implant and a tool for installing a rib and sternal implant, in accordance with an example of the present disclosure.

FIG. 5 shows an isometric view of implant 10 and tool 100, in accordance with an example of the present disclosure.

Implant 10 can include sternal implant 12, and rib link 14d. Sternal implant 12 can include superior portion 18, matrix 19, and inferior portion 20. Inferior portion 20 can include cartilage links 22. Rib link 14d can include proximal portion 28, strut 30, and distal portion 32. Each of proximal portions 28 can include proximal bores 34. Matrix 19 can include matrix bores 40. Tool 100 (lag tool) can include threaded portion 102, collar 104, and tool interface 106. Also shown in FIG. 5 are orientation identifiers superior, inferior, proximal, and distal.

Implant 10 can be connected and can operate consistently with FIGS. 1-4. However, FIG. 5 shows how tool 100 can interface with implant 10. Tool 100 can have a generally elongate body comprising a cylindrical geometric shape, in one example, and can have other geometric shapes in other examples. In one example, tool 100 can have a geometric shape of a hexagonal cylinder (apart from threaded portion 102), configured to engage a standard hex coupler or driver. Tool 100 can be comprised of any rigid material capable of transmitting torque, such as metals, plastics, and the like. In one example, tool 100 can be comprised of a stainless steel alloy.

Tool 100 can include collar 104 disposed near a distal termination of tool 100. Threaded portion 102 can extend from collar 104 to a distal termination of tool 100. Threaded portion 102 can be threaded to allow engagement with matrix bores 40 of matrix 19. Tool interface 106 can be a circumferential groove or channel disposed toward a distal termination of tool 100. Tool interface 106 can be used to secure tool 100 to a driver or other tool to transmit a torque to tool 100.

In operation of one example, rib link 14d can be placed near matrix 19. Then, threaded portion 102 can be inserted into one of proximal bores 34. Threaded portion 102 can thereafter be threaded into any selected bore of matrix bores 40. As tool 100 is threaded into an initial matrix bore 40, collar 104 will contact an anterior surface of proximal portion 28. As tool 100 is threaded further into the initial matrix bore 100, collar 104 will force or lag proximal portion 28 toward matrix 19 and will align proximal bores 34 with matrix bores 40 so that fasteners 16 can be inserted through the other proximal bores 34 and threadably engaged with the other matrix bores 40 to secure proximal portion 28 to matrix 19. After one, two, or three of fasteners 16 have been threaded through proximal bores 34 and into matrix bores 40, tool 100 can be unthreaded from the initial matrix bore 40 and removed, allowing another of fasteners 16 to be secured into the initial matrix bore 40 that received tool 100. Tool 100 can then be used to lag another of rib links 14 to matrix 19. Tool 100 can provide the benefit of easily lagging and aligning proximal portions 28 with matrix 19, which can save time and energy during an operation or procedure.

In some examples, a distal end, and/or other distal portion, of tool 100 can include a permanent magnet configured to magnetically couple to one or more of matrix bores 40 and proximal bores 34. This can allow proximal portion 28 to be more quickly lagged to matrix 19.

Figure 6:
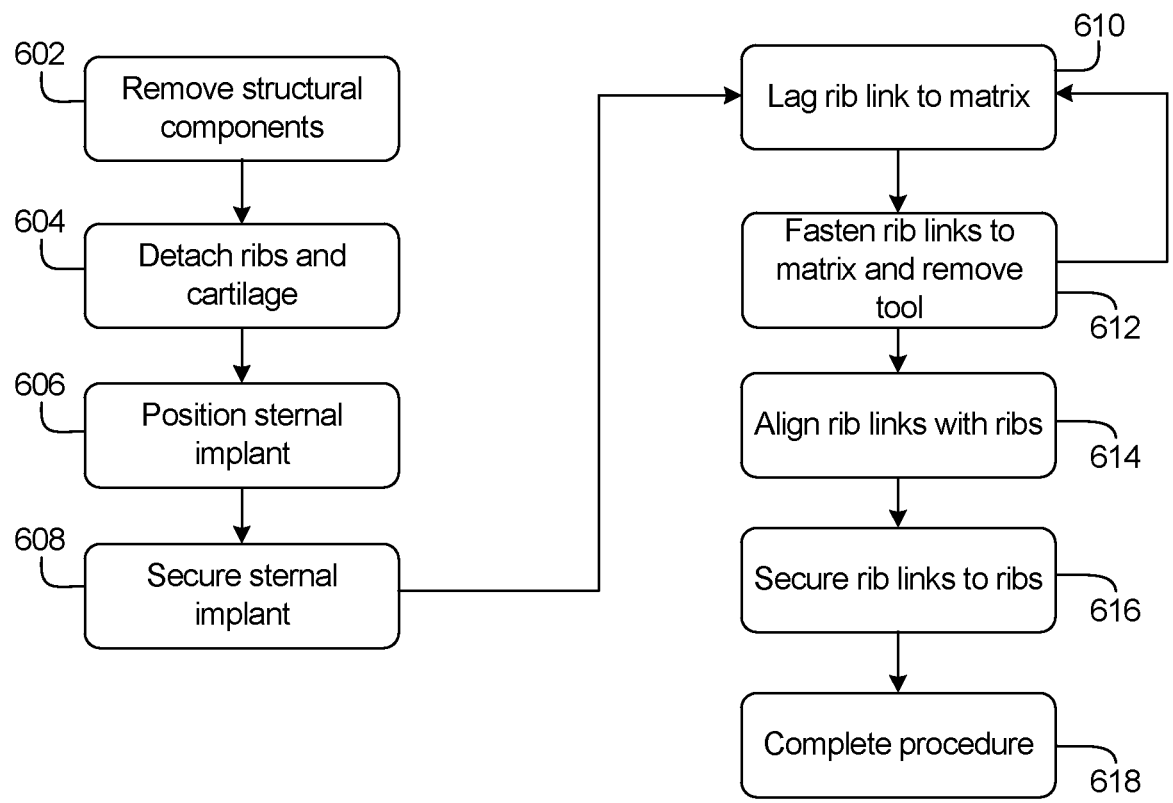
FIG. 6 shows a flow chart of a surgical procedure performed using a rib and sternal implant and tool, in accordance with an example of the present disclosure.

FIG. 6 shows a flow chart of a surgical procedure performed using implant 10 and tool 100, in accordance with an example of the present disclosure.

The steps or operations of the method of FIG. 6 are illustrated in a particular order for convenience and clarity; many of the discussed operations can be performed in a different sequence or in parallel, and some operations may be excluded, without materially impacting other operations. The method of FIG. 6, as discussed, includes operations performed by multiple different actors, devices, and/or systems. It is understood that subsets of the operations discussed in the method of FIG. 6 attributable to a single actor, device, or system could be considered a separate standalone process or method.

In operation of one example, a sternum, such as sternum 104 can be removed or resected in a procedure at step 602. Ribs 102 can also be resected or detached from sternum 104 at step 604. In some examples, manubrium 104 can be partially or fully removed from rib cage 100 at step 602. Also, cartilage 108 can be detached from sternum 104 at step 604.

After anatomical components have been removed, resected, and/or detached, step 606 can be performed, where sternal implant 12 is positioned to replace sternum 104. At step 608, sternal implant 12 can be secured at superior portion 18 to sternum 104 and/or manubrium 106 using bone fasteners. Also, at step 608, cartilage links 22 can be sutured to cartilage 108 and rib links 14 can be secured to ribs 102. Alternatively, cartilage links 22 can be sutured to cartilage 108 after rib links 14 are secured to sternal implant 12 and ribs 102. Rib links 14 can alternatively be secured to ribs 102 in later steps, as described below.

At step 610, tool 100 can be used to lag one of rib links 14 to matrix 19, so that fasteners 16 can be used to secure the rib link 14 to matrix 19. Tool 100 can then be removed so that fastening or securing can be completed for that rib link at step 612. The process of steps 610 and 612 can be repeated until all of rib links 14 are secured or coupled to sternal implant 12.

Step 614 can then be performed, where rib links 14 are aligned with ribs 102. In some cases, rib links will need to be bent at strut 30 to align rib links 14. In some other cases, alignment tabs 38 can be used to align rib links 14 with ribs 102. In some examples, steps 614 and 616 can be performed prior to steps 610 and 612, as desired by a physician. At step 616, distal portions 32 of rib links 14 can be secured to ribs 102 using bone fasteners that engage an anterior face of distal portions 32. At step 618, the procedure can be completed, which can include connecting other soft tissues, such as muscles, ligaments, cartilage, tendons, and bones, and can include closing the opening.

Additional Notes

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. An implant assembly comprising:
    a sternal implant couplable to a sternum and including a matrix portion comprising a plurality of matrix bores; and
    a rib link comprising:
        a distal portion couplable to a rib;
        a proximal portion including a plurality of rib link bores alignable with any of the plurality of matrix bores, the rib link bores and the matrix bores together configured to receive a fastener to secure the proximal portion to the matrix portion of the sternal implant; and
        a strut extending between the distal portion and the proximal portion.

2. The implant assembly of claim 1, wherein the sternal implant comprises:
    a superior portion located superior of the matrix portion, the superior portion securable to the sternum; and
    an inferior portion located interior of the matrix portion, the inferior portion securable to costal cartilage.

3. The implant assembly of claim 2, further comprising:
    a second rib link including a second proximal portion releasably couplable to the matrix portion of the sternal implant.

4. The implant assembly of claim 3, wherein the proximal portion and the second proximal portion are couplable to the matrix portion in a plurality of different configurations.

5. The implant assembly of claim 2, wherein the inferior portion of the sternal implant comprises:
    a cartilage link extending from the inferior portion, the cartilage link including a plurality of suture bores.

6. The implant assembly of claim 5, wherein the inferior portion of the sternal implant comprises:
    a second cartilage link extending from the inferior portion and including a second plurality of suture bores.

7. The implant assembly of claim 6, wherein the second cartilage link is releasably securable to the sternal implant using a fastener.

8. The implant assembly of claim 1, wherein the rib link comprises:
    an alignment tab extending from the distal portion and configured to at least partially engage the rib to align the distal portion with the rib.

9. The implant assembly of claim 1, wherein the distal portion comprises:
    a posterior surface comprising a patient-matched topography mateable with the rib.

10. The implant of claim 1, wherein the strut is configured to flex so that the distal portion can be aligned with the rib.

11. An implant assembly for a ribcage, the implant assembly comprising:
    a sternal implant couplable to a sternum of the ribcage and including a plurality of sternal implant bores; and
    a rib link comprising:
        a distal portion couplable to a rib of the ribcage; and
        a proximal portion connected to the distal portion, the proximal portion including a rib link bore alignable with any of the plurality of sternal implant bores to create an aligned pair configured to receive a fastener therethrough to secure the proximal portion to the sternal implant.

12. The implant assembly of claim 11, wherein the distal portion defines a plurality of bores configured to receive bone fasteners securable to the rib, the plurality of bores spaced over the distal portion to distribute stress transferred between the rib and the distal portion.

13. The implant assembly of claim 12, further comprising:
    a plurality of rib links including the rib link, each of the plurality of rib links releasably couplable to the sternal implant and to one of a plurality of ribs including the rib.

14. The implant assembly of claim 11, wherein the sternal implant comprises:
    a superior portion securable to the sternum; and
    an inferior portion securable to costal cartilage.

15. The implant assembly of claim 14, further comprising:
    a plurality of cartilage links each individually releasably securable to the sternal implant using a fastener.

16. The implant assembly of claim 15, wherein each of the plurality of cartilage links is configured to extend from the inferior portion of the sternal implant and is securable to costal cartilage.

17. An implant composing:
    a sternal implant couplable to a sternum and including a matrix portion comprising a plurality of matrix bores;
    a first rib link comprising:
        a first distal portion couplable to a first rib; and
        a first proximal portion couplable to the matrix portion of the sternal implant, the first proximal portion including a plurality of first rib link bores alignable with any of the plurality of matrix bores for receipt of a fastener therethrough; and
    a second rib link comprising:
        a second distal portion couplable to a second rib; and
        a second proximal portion couplable to the matrix portion of the sternal implant, the second proximal portion including a plurality of second rib link bores alignable with any of the plurality of matrix bores for receipt of a fastener therethrough;
    wherein each of the first and second rib links is securable to the matrix portion of the sternal implant in a plurality of different configurations utilizing various combinations of the plurality of matrix bores.

18. The implant of claim 17, wherein the sternal implant comprises:
   a superior portion located superior of the matrix portion, the superior portion securable to the sternum; and
   an inferior portion located inferior of the matrix portion, the inferior portion securable to costal cartilage.

19. The implant of claim 17, wherein the first rib link includes a first strut connecting the first distal portion to the first proximal portion, and wherein the second rib link includes a second strut connecting the second distal portion to the second proximal portion.

20. The implant of claim 19, wherein the strut comprises a cylindrical geometry configured to flex so that the distal portion can be aligned with the rib.

* * * * *

UNITED STATES PATENT AND TRADEMARK OFFICE
CERTIFICATE OF CORRECTION

PATENT NO. : 11,357,556 B2
APPLICATION NO. : 16/689587
DATED : June 14, 2022
INVENTOR(S) : Frank et al.

It is certified that error appears in the above-identified patent and that said Letters Patent is hereby corrected as shown below:

In the Claims

In Column 11, Line 51, in Claim 2, delete "interior" and insert --inferior-- therefor In Column 12, Line 49, in Claim 17, delete "composing:" and insert --comprising:-- therefor Signed and Sealed this
Sixteenth Day of August, 2022

Katherine Kelly Vidal
*Director of the United States Patent and Trademark Office*